(12) United States Patent
Lenormand et al.

(10) Patent No.: US 7,319,332 B2
(45) Date of Patent: Jan. 15, 2008

(54) METHOD FOR DETERMINING OF THE FORMATION FACTOR FOR A SUBTERRANEAN DEPOSIT FROM MEASUREMENTS ON DRILLING WASTE REMOVED THEREFROM

(75) Inventors: Roland Lenormand, Rueil Malmaison (FR); Patrick Egermann, Rueil Malmaison (FR); Joêlle Behot, Condecourt (FR)

(73) Assignee: Institut Francais du Petrole, Malmaison Cedex (FR)

( * ) Notice: Subject to any disclaimer, the term of this patent is extended or adjusted under 35 U.S.C. 154(b) by 111 days.

(21) Appl. No.: 10/554,598

(22) PCT Filed: Apr. 22, 2004

(86) PCT No.: PCT/FR2004/050169

§ 371 (c)(1),
(2), (4) Date: Oct. 27, 2005

(87) PCT Pub. No.: WO2004/097404

PCT Pub. Date: Nov. 11, 2004

(65) Prior Publication Data

US 2006/0248948 A1    Nov. 9, 2006

(30) Foreign Application Priority Data

Apr. 29, 2003   (FR) .................................. 03 05291

(51) Int. Cl.
*G01V 3/00* (2006.01)
*G01N 15/08* (2006.01)
(52) U.S. Cl. .......................................... 324/376; 73/38
(58) Field of Classification Search .................. 73/38, 73/152.23; 324/376
See application file for complete search history.

(56) References Cited

U.S. PATENT DOCUMENTS 2,583,284 A     1/1952  Wyllie et al.

(Continued)

FOREIGN PATENT DOCUMENTS

WO      WO 87/04790        8/1987

(Continued)

OTHER PUBLICATIONS

G.E. Archie, "The Electrical Resistivity Log As An Aid in Determining Some Reservoir Characteristics", Petroleum Development and Technology, vol. 146, 1942, pp. 54-62, XP008001923.

*Primary Examiner*—Hezron Williams
*Assistant Examiner*—John Fitzgerald
(74) *Attorney, Agent, or Firm*—Antonelli, Terry, Stout & Kraus, LLP.

(57) ABSTRACT

Method and device for determining the formation factor of underground zones from drill cuttings. The device comprises a cell (1) associated with a device for measuring the electrical conductivity of the cell with the content thereof. The cell containing the drill cuttings is filled with a first electrolyte solution (A) of known conductivity ($\sigma_A$). After saturation of the drill cuttings by first solution (A), the global electrical conductivity ($\sigma^*_A$) of the cell with the content thereof is determined. After discharging first solution (A), the cell containing the drill cuttings is filled with a second electrolyte solution (B) of known conductivity ($\sigma_B$), and the global electrical conductivity ($\sigma^*_B$) of the cell containing the second solution and the cuttings saturated with the first solution is determined. The cuttings formation factor (FF) is deduced therefrom by combination of the measurements.

14 Claims, 3 Drawing Sheets

U.S. PATENT DOCUMENTS

| | | | |
|---|---|---|---|
| 4,654,598 A | * | 3/1987 | Arulanandan et al. ...... 324/354 |
| 4,926,128 A | | 5/1990 | Givens |
| 4,979,393 A | * | 12/1990 | Leung et al. ............ 73/152.23 |
| 5,093,623 A | * | 3/1992 | Givens et al. ............... 324/376 |
| 5,105,154 A | * | 4/1992 | Givens et al. ............... 324/376 |
| 5,164,672 A | * | 11/1992 | Gilliland et al. ............ 324/376 |
| 5,209,104 A | | 5/1993 | Collins et al. |
| 5,417,104 A | * | 5/1995 | Wong ............................. 73/38 |
| 5,503,001 A | * | 4/1996 | Wong ............................. 73/38 |
| 5,610,524 A | * | 3/1997 | Longeron et al. ........... 324/376 |
| 5,679,885 A | * | 10/1997 | Lenormand et al. ........... 73/38 |
| 6,380,745 B1 | * | 4/2002 | Anderson et al. ........... 324/347 |
| 2005/0104596 A1 | * | 5/2005 | Fleury ....................... 324/376 |

FOREIGN PATENT DOCUMENTS

WO    WO 96/29616    9/1996

* cited by examiner

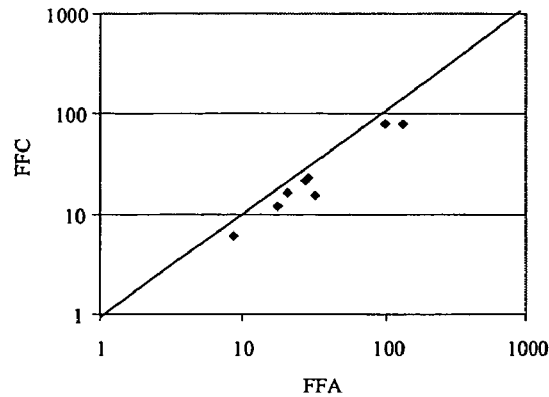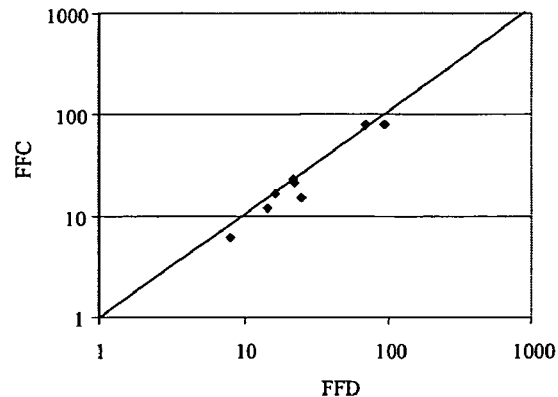
Fig.5A                                Fig.5B
| Ech | K (md) | φ (%) | FFA | FFD | FFC |
|---|---|---|---|---|---|
| V8 | 450.00 | 23.80 | 27.37 | 22.08 | 21.33 |
| Bri | 15.00 | 23.00 | 28.73 | 21.73 | 22.83 |
| Lav2 | 0.05 | 13.30 | 132.40 | 92.40 | 78.22 |
| GDV2 | 96.50 | 22.20 | 20.78 | 16.40 | 16.48 |
| LavJ | 515.00 | 27.90 | 17.71 | 14.43 | 11.92 |
| St Max | 1700.00 | 39.20 | 8.74 | 7.89 | 6.02 |
| Can1 | 0.31 | 11.30 | 99.11 | 69.63 | 79.75 |
| Berea | 230.00 | 19.70 | 31.87 | 24.66 | 15.32 |
Fig.6

METHOD FOR DETERMINING OF THE FORMATION FACTOR FOR A SUBTERRANEAN DEPOSIT FROM MEASUREMENTS ON DRILLING WASTE REMOVED THEREFROM

FIELD OF THE INVENTION

The present invention relates to a method and to a device for determining the formation factor of underground zones from rock cuttings taken to the surface during well drilling operations through underground reservoirs.

In the sphere of petrophysical characterization, there is a very important datum which conditions the interpretation of electric logs for evaluation of the water saturation in reservoirs: the factor referred to as Formation Factor (FF in short hereafter), which is defined as the ratio of the conductivity of a conducting liquid alone ($\sigma_w$) to the conductivity of the porous medium saturated with this conducting liquid ($\sigma_0$), i.e.:

$$FF = \frac{\sigma_w}{\sigma_0}.$$

Brine or another equivalent conducting liquid is preferably used as the conducting liquid.

Knowledge of this formation factor allows operating companies to obtain a first petrophysical characterization of a reservoir shortly after drilling the well and, consequently, good evaluation of the amounts of hydrocarbons in place.

BACKGROUND OF THE INVENTION

With current techniques, the formation factor is obtained by means of laboratory measurements on reservoir cores. These methods are expensive because of the cost of the coring operation and of the measurement itself, and the results are available only several months after drilling.

Acquisition of the experimental conductivity measurements on cores is based on a conventional material used in most petrophysics laboratories, and already implemented for example in patent FR-2,781,573 (U.S. Pat. No. 6,229,312) filed by the applicant, or in the following publication:

Sprunt, E. S., Maute, R. E., Rackers, C. I.: "An Interpretation of the SCA Electrical Resistivity", The Log Analyst, pp. 76-88, March-April 1990.

In order to overcome the high cost problem and the relatively long time required to obtain a measurement, techniques of calculating the formation factor from drill cuttings were developed. For example, U.S. Pat. No. 2,583,284 describes various methods for determining the formation factor from conductivity measurements carried out on drill cuttings. However, these techniques are very restricting on an experimental plane and the measurements relatively long to obtain.

SUMMARY OF THE INVENTION

The invention relates to a method of determining, in a simple and fast way, without the problems linked with the previous techniques, the formation factor of an underground zone from drill cuttings taken to the wellbore surface, comprising using a device including a cell (1) suited to contain cuttings and provided with electrodes connected to a device for measuring the conductivity of the cell content.

The method comprises at least the following stages:
cleaning said cuttings before setting them in the cell,
filling the cell with a first electrolyte solution (A) of known conductivity ($\sigma_A$) so as to saturate the cuttings with this first electrolyte solution (A),
measuring the global electrical conductivity ($\sigma^*_A$) of the cell with the content thereof,
discharging the first electrolyte solution (A) remaining between the cuttings from the cell,
filling the cell with a second electrolyte solution (B) of known conductivity ($\sigma_B$),
determining the global electrical conductivity ($\sigma^*_B$) of the cell containing second electrolyte solution (B) and the cuttings saturated with first electrolyte solution (A),
deducing therefrom the cuttings formation factor (FF) from the previous measurements.

According to the invention, the cuttings can be saturated with carbon dioxide by injection of this gas into the cell, prior to filling the cell with first electrolyte solution (A).

The electrolyte solutions can be brines of different concentrations, the concentration and the conductivity of first electrolyte solution (A) can be higher than those of second solution (B).

According to the invention, first electrolyte solution (A) remaining between the cuttings can be discharged from the cell by gravity draining.

First electrolyte solution (A) can also be discharged by injection of air. In this case, the pressure of the air injected can be determined according to the pore size of the cuttings.

In the case of gravity draining, it can be improved by capillary desorption.

Capillary desorption can be carried out by means of a semipermeable membrane allowing passage of the first electrolyte solution but not of the air.

Finally, according to the invention, the formation factor can be determined from the mean field theory.

The invention also relates to a device for implementing the method described above. This device comprises:
means of saturating the cuttings contained in the cell with $CO_2$,
means intended for fast draining of the electrolyte solution contained between the cuttings.

According to the invention, said draining means of the device can include a semipermeable membrane, permeable to the brine and impermeable to air.

BRIEF DESCRIPTION OF THE FIGURES

Other features and advantages of the invention will be clear from reading the description hereafter, with reference to the accompanying figures wherein:

FIG. 5A shows, in form of a crossed diagram, the results obtained with the self-similar approach, FIG. 5B shows, in form of a crossed diagram, the results obtained with the derivative approach, and FIG. 6 shows a comparative table of the results obtained with the two methods considered (self-similar and derivative) from the cuttings and with the reference measurements obtained from experiments on cores.

DETAILED DESCRIPTION

The method according to the invention, intended for fast determination of the FF from drill cuttings, is based on the acquisition of experimental data obtained by measuring the conductivity of the cuttings under various conditions. When measuring the electrical conductivity of a cell containing rock fragments, the conductivity depends on the conductivity of the rock fragments and of the liquid contained between the fragments. The method provided allows to interpret the experimental measurements in terms of FF using theoretical models. Two application instances are provided. They show the very good agreement between the FF values obtained from cores and the FF values obtained from fragments of these cores over a wide FF range.

The invention provides a method and a device allowing fast and rigorous calculation of the formation factor by means, among other things, of conductivity measurements performed with two conducting liquids that can be miscible.

According to an embodiment of the invention, the two miscible conducting liquids used are brines of different concentrations:

liquid A: brine with a 75 g/l salt concentration, which corresponds to a conductivity of 9.88 $(Ohm.m)^{-1}$, liquid B: brine with a 25 g/l salt concentration, which corresponds to a conductivity of 3.81 $(Ohm.m)^{-1}$ and gives a conductivity contrast of a factor 3 approximately.

Brine is understood to be an electrolyte solution allowing conductivity measurements to be readily obtained.

The general principle of the method according to the invention is based on the measurement of four conductivities:

1. The conductivity of the first electrolyte solution ($\sigma_A$)
2. The conductivity of the cell filled with the first electrolyte solution and the cuttings saturated with this first solution ($\sigma^*_A$)
3. The conductivity of the second electrolyte solution ($\sigma_B$)
4. The conductivity of the cell filled with the second electrolyte solution and the cuttings saturated with the first solution ($\sigma^*_B$).

Experimental Data Acquisition

Figure 1:
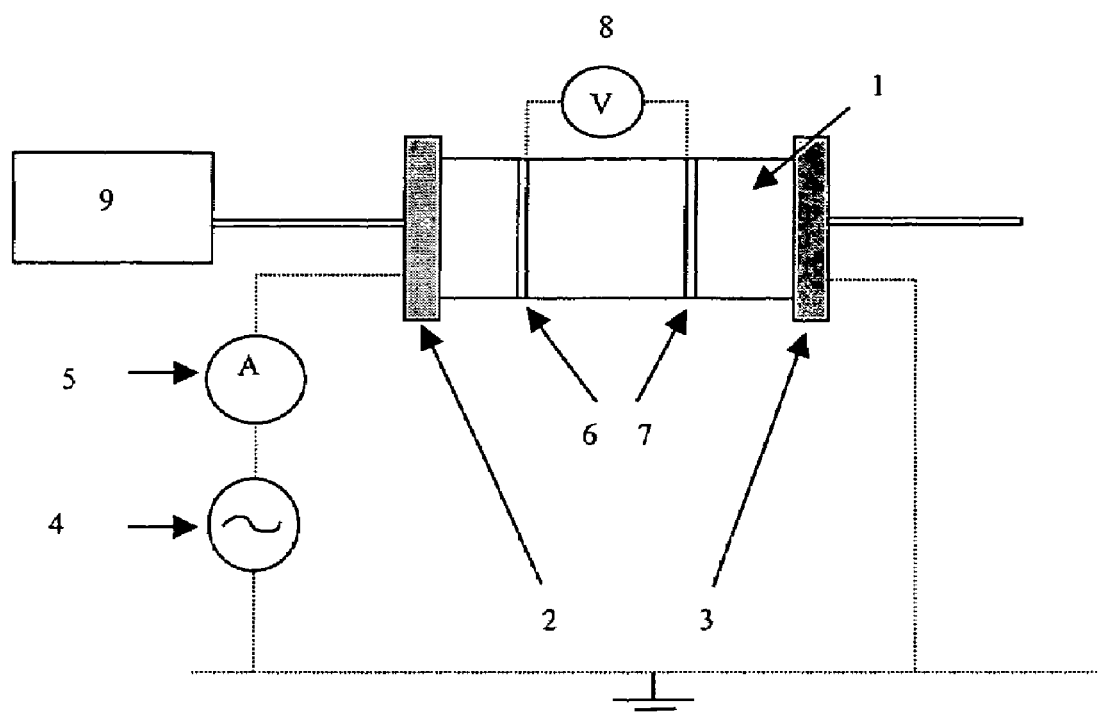
FIG. 1 diagrammatically shows a conductivity measuring device with four electrodes.

The device allowing acquisition of the measurements within the scope of the implementation of the invention is diagrammatically shown in FIG. 1. It mainly consists of a 3-cm long containment cell (1) of circular surface area 9.48 $cm^2$, which gives a total volume of about 30 $cm^3$. This corresponds to approximately 15 $cm^3$ rock once the cell filled. This cell is made of a non-conducting material. It is closed at the opposite ends thereof by two end parts 2, 3 made of a conducting material. A variable-frequency generator 4 is connected between end parts 2, 3 and the current applied thereby is measured by an ammeter 5. Electrodes 6, 7 connected to a voltmeter 8 are arranged at two points spaced out along the body of cell 1. A pump 9 allows liquids to be fed into the cell.

Cell 1 is first filled with the drill cuttings, previously cleaned and dried, and carbon dioxide until saturation of the cuttings with carbon dioxide is obtained. The volume of gas injected is such that all the pores of the cuttings are filled with carbon dioxide. The goal of this operation is to improve the saturation of the cuttings by the brine by means of the mechanisms of diffusion of the $CO_2$ in the air and of dissolution of the $CO_2$ in the brine, and not by air vacuum, which is more difficult to achieve.

Figure 2:
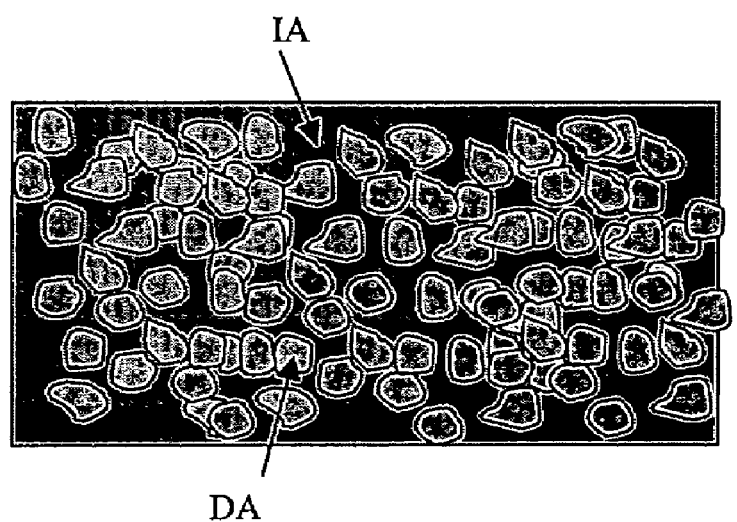
FIG. 2 illustrates state A first obtained by filling the cell containing the drill cuttings with a first liquid A.

The cell is thereafter completely filled with a conducting liquid A (a brine of known concentration and therefore known conductivity) till complete saturation of the cuttings by dissolution of the $CO_2$ in the brine, and the global conductivity of the cell and of the content thereof, denoted by $\sigma^*_A$, is measured. This state, referred to as state A, is shown in FIG. 2 where IA represents liquid A in the inter-cuttings space and DA represents liquid A in the cuttings.

Liquid A is then discharged by gravity draining and under air pressure (or under brine underpressure). The pressure to be exerted depends on the maximum size of the cuttings pores. In fact, too high a pressure would desaturate, even partly, the cuttings. This pressure should therefore be neither too high (partial desaturation of the cuttings) nor too low to limit the presence of liquid A in the inter-cuttings space. It can be readily calculated from Laplacian formulas.

In order to facilitate drainage of the inter-cuttings brine while keeping the cuttings saturated, it is also possible to carry out in addition capillary desorption of the inter-cuttings space occupied by liquid A, by means of a semi-permeable membrane. Drainage of the inter-cuttings brine is then controlled by the presence of this membrane which allows passage of the brine but not of the air. An air pressure is applied to the cell so as to drive the inter-cuttings brine out without desaturating the rock. A 10-mbar pressure (that can be controlled by a water level imposed in a 10-cm capillary) then provides good drainage of the inter-cuttings space without desaturating the rock, and over a wide permeability range (the air must not be able to enter the largest existing pore of the porous medium whose size corresponds to what is referred to as the input pressure).

Then, after this fast (air pressure-assisted gravity drainage) and efficient draining (use of a semipermeable membrane and of an air pressure), the cell is filled with another conducting liquid B (brine of lower concentration than brine A) without changing the nature of the liquid (brine A) saturating the cuttings.

The measurements have to be achieved before diffusion of liquid B occurs in the pores of the cuttings by modifying the saturation.

Figure 4:
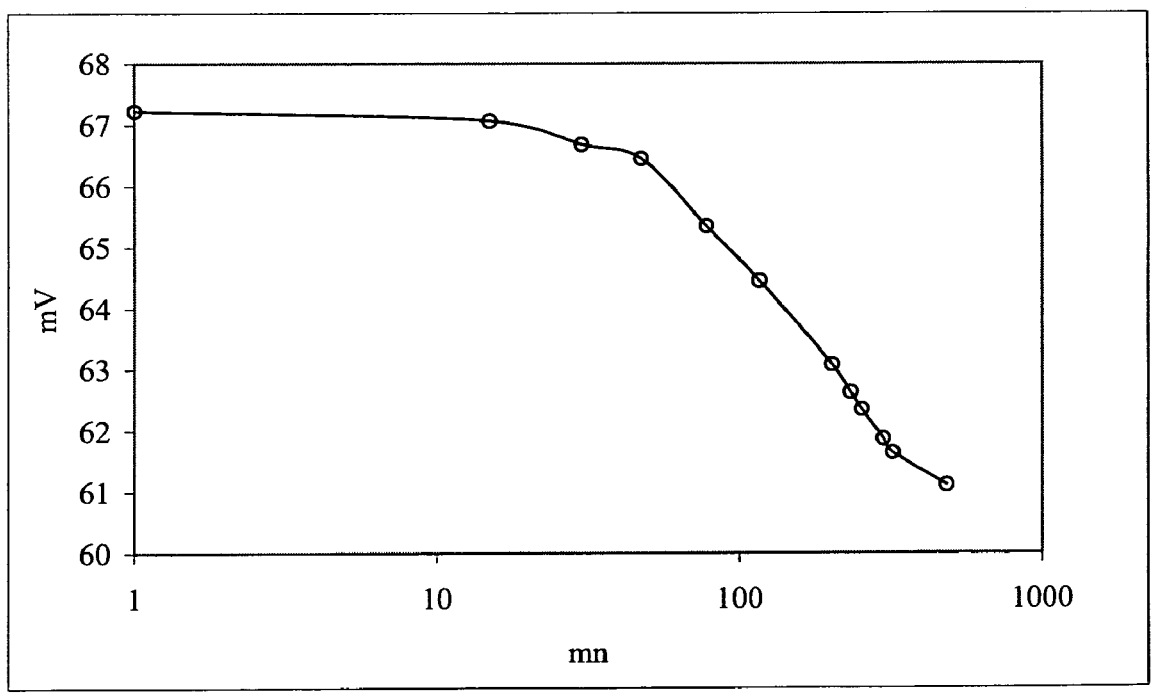
FIG. 4 illustrates experimental data showing a long-time conductivity signal drift after a draining operation.

In practice, the time available for measurements is deduced from the comparison between the diffusion time and the drainage time. FIG. 4 illustrates experimental data showing a long-time (in mn on the abscissa axis) drift of the conductivity signal (voltage in mV on the ordinate axis) after a draining operation (t=0). It clearly shows that the effect (voltage drop) of the diffusion of the inter-cuttings brine is not a fast phenomenon. More than one hour is required before a notable effect can be observed on the results. FIG. 4 therefore confirms that fast draining techniques are operational for applying the method to two miscible liquids.

Figure 3:
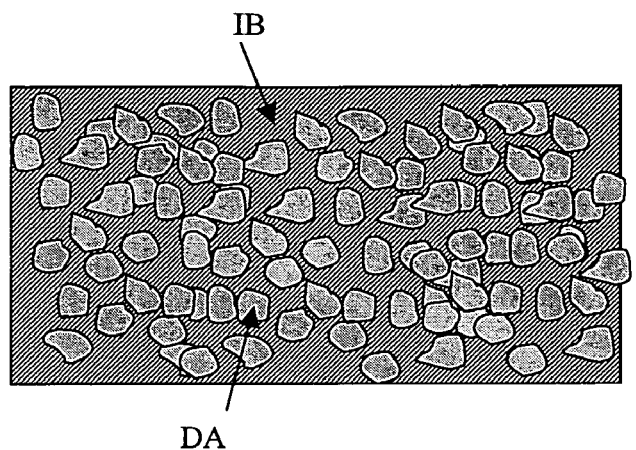
FIG. 3 illustrates state B obtained thereafter after changing liquid A for another liquid B.

At the end of this stage, cuttings saturated with liquid A thus soak in a liquid B. The global conductivity of the system, denoted by $\sigma^*_B$, is then measured. This stage, referred to as state B, is shown in FIG. 3 where IB represents liquid B in the inter-cuttings space and DA liquid A in the cuttings. Furthermore, the cuttings have not been removed from the cell during draining and filling with second liquid B, which allows to keep the shape of the porous medium and thus to make the measurements more reliable (equivalent measurements between state A and state B). The two liquids used being brines, no particular experimental precaution has to be considered.

If brines of known salinity such as liquids A and B are used, the value of their conductivity can be deduced from tables such as those that can be found in the following publication:

Worthington A. E., Hedges J. H., Pallatt N.: "SCA Guidelines for sample preparation and porosity measurement of electrical resistivity samples", The Log Analyst, pp. 20-28, January-February 1990.

In a more general case, it is also possible to directly measure the value of the conductivity of liquids A and B by means of a conductimeter. $\sigma_A$ and $\sigma_B$ thus represent the conductivities of liquids A and B alone.

In the procedure used, it is advantageous to use first the more salted and the more conducting brine, and to replace the inter-cuttings space by the less salted brine. This allows to keep the more conducting liquid in the rock so as to favour the accuracy of the FF measurement.

Experimental Results Interpretation in Terms of FF

We consider that the whole of the volume is occupied by 2 types of media 1 and 2. The volume fraction of medium 1 is denoted by x and the volume fraction of medium 2 by y, equal to 1-x. We consider throughout the description hereafter that medium 1 represents inter-cuttings liquid A or B, and medium 2 the saturated rock cuttings. The conductivities of each medium, inter-cuttings liquid and saturated rock cuttings, are denoted by $\sigma_1$ and $\sigma_2$, and the global conductivity of the system is denoted by $\sigma^*$.

In order to take account of the mixed character of the two media, the method according to the invention has been implemented from techniques resulting from the mean field theory as described in the following publications:

Berryman J. G.: "Mixture Theories for Rock Properties", Rock Physics and Phase Relation, pp. 205-228, 1990, or Bruggeman D. A. G.: "Berechnung verschiedener physikalischer Konstanten von heterogenen Substanzen", Ann. Physik.(Leipzig), 24, 636-679, 1935.

Any other method taking account of this "mixed" character could be used without departing from the scope of the invention.

According to a first approach referred to as self-similar, the following relation can be written:

$$h(x) \times \frac{\sigma_1 - \sigma^*}{\sigma_1 + 2\sigma^*} + f(y) \times \frac{\sigma_2 - \sigma^*}{\sigma_2 + 2\sigma^*} = 0$$

with: $h(x) = 1 - f(y)$ where h and $f$ are functions of the volume fractions taking account of the shape of the grains that make up the cuttings. For example, in the case of spherical grains, we have the following relation: $f = y^L$ with $L = \frac{1}{3}$.

$$\text{i.e.} (1 - f(y)) \times \frac{\sigma_1 - \sigma^*}{\sigma_1 + 2\sigma^*} + f(y) \times \frac{\sigma_2 - \sigma^*}{\sigma_2 + 2\sigma^*} = 0 \quad (1)$$

We can then write the previous equation for the two experimentally measured states (A and B):

State A:

$$\sigma_1 = \sigma_A \quad (2)$$
$$\sigma_2 = \frac{\sigma_A}{FF} \quad \sigma^* = \sigma_A^*$$

$$(1 - f(y)) \times \frac{\sigma_A - \sigma_A^*}{\sigma_A + 2\sigma_A^*} + f(y) \times \frac{\frac{\sigma_A}{FF} - \sigma_A^*}{\frac{\sigma_A}{FF} + 2\sigma_A^*} = 0$$

State B:

$$\sigma_1 = \sigma_B \quad (3)$$
$$\sigma_2 = \frac{\sigma_A}{FF} \quad \sigma^* = \sigma_B^*$$

$$(1 - f(y)) \times \frac{\sigma_B - \sigma_B^*}{\sigma_B + 2\sigma_B^*} + f(y) \times \frac{\frac{\sigma_A}{FF} - \sigma_B^*}{\frac{\sigma_A}{FF} + 2\sigma_B^*} = 0$$

Equations (2) and (3) can also be written as follows:

$$f(y) = \frac{1}{1 - \left(\frac{\frac{\sigma_A}{FF} - \sigma_A^*}{\frac{\sigma_A}{FF} + 2\sigma_A^*}\right) \times \frac{\sigma_A + 2\sigma_A^*}{\sigma_A - \sigma_A^*}} \quad (4)$$

$$f(y) = \frac{1}{1 - \left(\frac{\frac{\sigma_A}{FF} - \sigma_B^*}{\frac{\sigma_A}{FF} + 2\sigma_B^*}\right) \times \frac{\sigma_B + 2\sigma_B^*}{\sigma_B - \sigma_B^*}} \quad (5)$$

The functions allowing to take account of the shape of the grains (h and $f$) are unknown and difficult to estimate. The interest of performing the measurements with two inter-cuttings liquids then clearly appears: the combination of Equations (4) and (5) allows unknown $f(y)$ to be removed.

In fact, by combining Equations (4) and (5), we obtain:

$$\left(\frac{\frac{\sigma_A}{FF} - \sigma_A^*}{\frac{\sigma_A}{FF} + 2\sigma_A^*} \times \frac{\sigma_A + 2\sigma_A^*}{\sigma_A - \sigma_A^*}\right) = \left(\frac{\frac{\sigma_A}{FF} - \sigma_B^*}{\frac{\sigma_A}{FF} + 2\sigma_B^*} \times \frac{\sigma_B + 2\sigma_B^*}{\sigma_B - \sigma_B^*}\right) \quad (6)$$

By putting $$K_A = \left(\frac{\sigma_A + 2\sigma_A^*}{\sigma_A - \sigma_A^*}\right)$$

$$K_B = \left(\frac{\sigma_B + 2\sigma_B^*}{\sigma_B - \sigma_B^*}\right)$$

$$X = \frac{\sigma_A}{FF},$$

we obtain a second-degree equation that we can solve analytically, $$(K_B - K_A)X^2 + [K_B(2\sigma_A^* - \sigma_B) - K_A(2\sigma_B^* - \sigma_A)]X + 2\sigma_A^*\sigma_B^*(K_A - K_B) = 0 \quad (7)$$

Solution of this equation always gives two real roots because the discriminant is always strictly positive, $$\text{Delta} = [K_B(2\sigma_A^* - \sigma_B^*) - K_A(2\sigma_B^* - \sigma_A^*)]^2 + 8\sigma_A^*\sigma_B^*(K_B - K_A)^2 \quad (8)$$

$$FF = \frac{2(K_B - K_A)\sigma_A}{-(K_B(2\sigma_A^* - \sigma_B^*) - K_A(2\sigma_B^* - \sigma_A^*)) \pm \sqrt{\text{Delta}}}$$

Between the two solutions, only the solution that is physically acceptable is kept (FF>0).

According to a second procedure, a derivative approach is used and the following relation between $\sigma_1$ (conductivity of the inter-cuttings space), $\sigma_2$ (conductivity of the cuttings) and $\sigma^*$ (global conductivity of the system) can be written:

$$\left(\frac{\sigma_2 - \sigma^*}{\sigma_2 - \sigma_1}\right)\left(\frac{\sigma_1}{\sigma^*}\right) = 1 - f(y) \quad (11)$$

The previous equation can be applied for the two experimentally measured states (A and B):

State A:

$$\sigma_1 = \sigma_A \quad (12)$$
$$\sigma_2 = \frac{\sigma_A}{FF} \quad \sigma^* = \sigma_A^*$$
$$\left(\frac{\frac{\sigma_A}{FF} - \sigma_A^*}{\frac{\sigma_A}{FF} - \sigma_A}\right)\left(\frac{\sigma_A}{\sigma_A^*}\right) = 1 - f(y)$$

State B:

$$\sigma_1 = \sigma_B \quad (13)$$
$$\sigma_2 = \frac{\sigma_A}{FF} \quad \sigma^* = \sigma_B^*$$
$$\left(\frac{\frac{\sigma_A}{FF} - \sigma_B^*}{\frac{\sigma_A}{FF} - \sigma_B}\right)\left(\frac{\sigma_B}{\sigma_B^*}\right) = 1 - f(y)$$

By combining Equations (12) and (13), we directly obtain a relation where the only unknown is FF:

$$\left(\frac{\sigma_A/FF - \sigma_A^*}{\sigma_A/FF - \sigma_A}\right)\left(\frac{\sigma_A}{\sigma_A^*}\right) = \left(\frac{\sigma_A/FF - \sigma_B^*}{\sigma_A/FF - \sigma_B}\right)\left(\frac{\sigma_B}{\sigma_B^*}\right) \quad (14)$$

If we now put $$K_A = \left(\frac{\sigma_A}{\sigma_A^*}\right), K_B = \left(\frac{\sigma_B}{\sigma_B^*}\right) \text{ and } X = \sigma_A/FF,$$

we obtain a second-degree equation in X, $$(K_A - K_B)X^2 - [K_A(\sigma^*_A + \sigma_B) - K_B(\sigma^*_B + \sigma_A)]X + K_A\sigma^*_A\sigma_B + K_B\sigma^*_B\sigma_A = 0 \quad (15)$$

The discriminant of this equation is as follows:

$$\text{Delta}[K_A(\sigma^*_A - \sigma_B) - K_B(\sigma^*_B - \sigma_A)]^2 + 4K_AK_B(\sigma^*_B - \sigma^*_A)(\sigma_A - \sigma_B)$$

and leads to two real solutions among which only the acceptable physical solution (FF>0) is kept:

$$FF = \frac{2(K_A - K_B)\sigma_A}{(K_A(\sigma^*_A + \sigma_B) - K_B(\sigma^*_B + \sigma_A)) \pm \sqrt{\text{Delta}}} \quad (16)$$

Validation of the Method by Comparison with Reference Measurements

A series of experiments was carried out from rocks of various permeabilities and porosities in order to compare the results obtained with cuttings according to the two procedures described above with measurements obtained by means of a conventional procedure using a core.

The results are given in the crossed diagrams of FIGS. 5A and 5B, where the ordinate axis represents the value of the FFT measured on core (FFC) and the abscissa axis the value of the FF measured on cuttings with the self-similar method (FFA) and the derivative method (FFD) respectively. The table of FIG. 6 groups these results for various samples (Ech) having different permeabilities (K) and porosities ($\phi$). These results show a very good correlation between the reference measurements and the measurements on cuttings. Of the two approaches considered, self-similar or derivative, it appears that the second one gives the best results.

It has to be pointed out that the calculation methods referred to as "self-similar" and "derivative", which were used to determine the formation factor according to the present invention, are described here by way of non limitative examples.

The invention claimed is:

1. A method of determining the formation factor of an underground zone from drill cuttings taken to the wellbore surface, wherein a device including a cell suited to contain cuttings and provided with electrodes connected to a device for measuring the conductivity of the cell content is used, the method comprising at least the following stages:

cleaning said cuttings before setting them in the cell, filling the cell with a first electrolyte solution of known conductivity ($\sigma_A$) so as to saturate the cuttings with this first electrolyte solution, measuring the global electrical conductivity ($\sigma^*_A$) of the cell with the content thereof, discharging the first electrolyte solution remaining between the cuttings from the cell, filling the cell with a second electrolyte solution of known conductivity ($\sigma_B$), determining the global electrical conductivity ($\sigma^*_B$) of the cell containing second electrolyte solution and the cuttings saturated with first electrolyte solution, deducing therefrom the cuttings formation factor from the previous conductivity measurements and known conductivities of the first and second electrolyte solutions.

2. A method as claimed in claim 1, wherein the electrolyte solutions are brines of different concentrations.

3. A method as claimed in claim 1, wherein the concentration and the conductivity of first electrolyte solution are higher than those of second solution.

4. A method as claimed in claim 1, wherein the formation factor is determined from the mean field theory.

5. A method of determining the formation factor of an underground zone from drill cuttings taken to the wellbore surface, wherein a device including a cell suited to contain cuttings and provided with electrodes connected to a device for measuring the conductivity of the cell content is used, the method comprising at least the following stages:

cleaning said cuttings before setting them in the cell,
saturating the cuttings with carbon dioxide by injection of this gas into the cell, then
filling the cell with a first electrolyte solution of known conductivity ($\sigma_A$) so as to saturate the cuttings with this first electrolyte solution,
measuring the global electrical conductivity ($\sigma^*_A$) of the cell with the content thereof,
discharging the first electrolyte solution remaining between the cuttings from the cell,
filling the cell with a second electrolyte solution of known conductivity ($\sigma_B$),
determining the global electrical conductivity ($\sigma^*_B$) of the cell containing second electrolyte solution and the cuttings saturated with first electrolyte solution,
deducing therefrom the cuttings formation factor from the previous measurements.

6. A method of determining the formation factor of an underground zone from drill cuttings taken to the wellbore surface, wherein a device including a cell suited to contain cutting and provided with electrodes connected to a device for measuring the conductivity of the cell content is used, the method comprising at least the following stages:
cleaning said cuttings before setting them in the cell,
filling the cell with a first electrolyte solution of known conductivity ($\sigma_A$) so as to saturate the cuttings with this first electrolyte solution,
measuring the global electrical conductivity ($\sigma^*_A$) of the cell with the content thereof,
discharging the first electrolyte solution remaining between the cuttings from the cell by gravity draining,
filling the cell with a second electrolyte solution of known conductivity ($\sigma_B$),
determining the global electrical conductivity ($\sigma^*_B$) of the cell containing second electrolyte solution and the cuttings saturated with first electrolyte solution,
deducing therefrom the cuttings formation factor from the previous measurements.

7. A method as claimed in claim 6, wherein first electrolyte solution is discharged by air injection.

8. A method as claimed in claim 7, wherein the pressure of the air injected is determined according to the pore size of the cuttings.

9. A method as claimed in claim 6, wherein gravity drainage is improved by capillary desorption.

10. A method as claimed in claim 9, wherein capillary desorption is carried out by means of a semipermeable membrane allowing passage of the first electrolyte solution but not of air.

11. A device for implementing a method of determining the formation factor of an underground zone from drill cuttings taken to the wellbore surface, wherein a device including a cell suited to contain cuttings and provided with electrodes connected to a device for measuring the conductivity of the cell content is used, the method comprising at least the following stages: cleaning said cuttings before setting them in the cell, filling the cell with a first electrolyte solution of known conductivity ($\sigma_A$) so as to saturate the cuttings with this first electrolyte solution, measuring the global electrical conductivity ($\sigma^*_A$) of the cell with the content thereof, discharging the first electrolyte solution remaining between the cuttings from the cell, filling the cell with a second electrolyte solution of known conductivity ($\sigma_B$), determining the global electrical conductivity ($\sigma^*_B$) of the cell containing second electrolyte solution and the cuttings saturated with first electrolyte solution, deducing therefrom the cutting formation factor from the previous measurements, characterized in that the device comprises:
means of saturating the cuttings contained in the cell with $CO_2$,
means intended for fast draining of the electrolyte solution contained between the cuttings.

12. A device as claimed in claim 11, wherein said draining means comprise a semipermeable membrane permeable to the brine and impermeable to air.

13. A method of determining the formation factor of an underground zone from drill cuttings taken to the wellbore surface, wherein a device including a cell suited to contain cuttings and provided with electrodes connected to a device for measuring the conductivity of the cell content is used, the method comprising at least the following stages:
cleaning said cuttings before setting them in the cell,
filling the cell with a first electrolyte solution of known conductivity ($\sigma_A$) so as to saturate the cuttings with this first electrolyte solution,
measuring the global electrical conductivity ($\sigma^*_A$) of the cell with the content thereof,
discharging the first electrolyte solution remaining between the cuttings from the cell by air injection,
filling the cell with a second electrolyte solution of known conductivity ($\sigma_B$),
determining the global electrical conductivity ($\sigma^*_B$) of the cell containing second electrolyte solution and the cuttings saturated with first electrolyte solution,
deducing therefrom the cuttings formation factor from the previous measurements.

14. A method as claimed in claim 13, wherein the pressure of the air injected is determined according to the pore size of the cuttings.

* * * * *